(12) United States Patent
Thom et al.

(10) Patent No.: US 7,191,664 B2
(45) Date of Patent: Mar. 20, 2007

(54) TESTING OF MECHANICAL PROPERTIES OF MATERIALS

(75) Inventors: Nicholas Howard Thom, Nottingham (GB); Jonathon Paul Edwards, Nottingham (GB)

(73) Assignee: Scott Wilson Pavement Engineering Limited, Chilwell (GB)

( * ) Notice: Subject to any disclaimer, the term of this patent is extended or adjusted under 35 U.S.C. 154(b) by 0 days.

(21) Appl. No.: 11/032,901

(22) Filed: Jan. 11, 2005

(65) Prior Publication Data

US 2005/0178211 A1 Aug. 18, 2005

(30) Foreign Application Priority Data

Jan. 13, 2004 (GB) ................ 0400632.6

(51) Int. Cl.
*G01N 3/08* (2006.01)
(52) U.S. Cl. ............... 73/820; 73/805; 73/818; 73/819; 73/823; 73/825; 73/865.6
(58) Field of Classification Search ............. 73/820, 73/865.6, 818, 823, 825
See application file for complete search history.

(56) References Cited

U.S. PATENT DOCUMENTS

| | | | |
|---|---|---|---|
| 4,554,868 A * | 11/1985 | Zimmer ............. | 100/229 R |
| 4,562,726 A * | 1/1986 | Barnaby ............. | 73/38 |
| 4,697,457 A * | 10/1987 | Fochtman et al. ..... | 73/820 |
| 4,854,175 A | 8/1989 | Budhu | |
| 4,905,521 A | 3/1990 | Wagner et al. | |
| 5,606,133 A * | 2/1997 | Hines et al. ......... | 73/824 |
| 5,677,495 A * | 10/1997 | Johnson et al. ...... | 73/856 |
| 5,712,431 A * | 1/1998 | Vilendrer ........... | 73/841 |
| 5,817,946 A * | 10/1998 | Brovold ............ | 73/818 |
| 5,939,642 A * | 8/1999 | King et al. .......... | 73/813 |
| 5,948,218 A * | 9/1999 | Kheder et al. ....... | 204/196.33 |
| 6,598,486 B2 * | 7/2003 | Vilendrer et al. ..... | 73/841 |
| 6,857,322 B2 * | 2/2005 | Garcin et al. ........ | 73/818 |
| 2003/0075820 A1 * | 4/2003 | Hines ............... | 264/40.1 |
| 2004/0123685 A1 * | 7/2004 | Pyle et al. .......... | 73/865.9 |
| 2004/0244497 A1 * | 12/2004 | Abdel-Hadi et al. ... | 73/819 |
| 2005/0022608 A1 * | 2/2005 | Moscrip ............ | 73/818 |
| 2005/0191758 A1 * | 9/2005 | Pether et al. ........ | 436/174 |

FOREIGN PATENT DOCUMENTS

GB 2 258 734 A 2/1993
WO WO 2004/019010 A1 3/2004

* cited by examiner

*Primary Examiner*—Edward Lefkowitz
*Assistant Examiner*—Freddie Kirkland, III
(74) *Attorney, Agent, or Firm*—Nixon Peabody LLP

(57) ABSTRACT

Apparatus is disclosed for testing the mechanical properties of a material. The apparatus comprises a sample container (10) adapted to be filled with a sample of the material, and a housing (20) within which the sample container (10) is, in use, fixedly mounted. The sample container (10) has a first, open face via which a compressive load can be applied to the sample and a second face (19) disposed orthogonally to the first, open face. At least a portion of the second face (19) is resiliently displaceable, outwardly of the sample container (10), in response to deformation of the sample brought about by application of the load.

41 Claims, 5 Drawing Sheets

TESTING OF MECHANICAL PROPERTIES OF MATERIALS

BACKGROUND AND SUMMARY

This application claims the priority benefit of U.K. Patent Application 0400632.6, filed Jan. 13, 2004, which is hereby incorporated by reference in its entirety.

This invention relates to the testing of mechanical properties of materials, and in particular to the testing of mechanical properties of materials for use in pavement construction. By "pavement" in this context is meant particularly surfaces intended to provide a carriageway or hard standing for vehicles, eg roadways, car parks, airport runways and taxiways, and the like.

Roads and other forms of pavement are commonly constructed using quarried aggregate that is compacted and optionally bound using a suitable binder, such as cement or bitumen. It is clearly desirable to be able to test the mechanical properties of such materials in order to ensure that the material being tested is suitable for its intended application. It may also be desirable to test samples of material taken from an existing pavement in order to monitor the performance of the pavement.

One established method for testing the mechanical properties of samples of bound aggregate, such as asphalt, uses apparatus known as the Nottingham Asphalt Tester, which is described, for example, by S F Brown in *Proc. Instn Civ. Engrs Transp.*, (1995), 111, November, pp 289–297. However, apparatus such as the Nottingham Asphalt Tester may not be suitable for testing the mechanical properties of unbound or lightly-bound aggregates.

The mechanical properties of unbound and lightly-bound road construction materials are presently investigated either in situ using dynamic plate testing, which requires a full-scale pavement section to be constructed, or in a laboratory using a repeated load triaxial test, which is a relatively complicated and expensive procedure that is presently only practicable in universities and research establishments.

There is therefore a need for material testing apparatus that is simple and inexpensive to operate but generates a useful set of data regarding the relevant mechanical properties of unbound or lightly-bound aggregate for use in road construction.

There has now been devised an improved apparatus and an improved method for the testing of mechanical properties of a material, which overcome or substantially mitigate the above-mentioned and/or other disadvantages associated with the prior art.

According to a first aspect of the invention, there is provided apparatus for testing the mechanical properties of a material, which apparatus comprises a sample container adapted to be filled with a sample of the material, and a housing within which the sample container is, in use, fixedly mounted, the sample container having a first, open face via which a compressive load can be applied to the sample and a second face disposed orthogonally to the first, open face, at least a portion of said second face being resiliently displaceable, outwardly of the sample container, in response to deformation of the sample brought about by application of the load.

According to a further aspect of the invention, there is provided a sample container for use in testing the mechanical properties of a material, the sample container being adapted to be filled with a sample of the material, and having a first, open face via which a compressive load can be applied to the sample and a second face disposed orthogonally to the first, open face, at least a portion of said second face being displaceable, outwardly of the sample container, in response to deformation of the sample.

According to a further aspect of the invention, there is provided a method of testing the mechanical properties of a material, which method comprises the following steps:
(a) providing apparatus as described above;
(b) introducing a sample of the material into the sample container;
(c) engaging the sample container with the housing;
(d) applying a compressive force to the sample; and
(e) measuring movement of the resiliently-displaceable second face, or resiliently-displaceable portion thereof, in response to said compressive force.

The apparatus and method according to the invention are advantageous principally because the mechanical properties of many different materials, including unbound and lightly-bound aggregate, can be accurately investigated in a simple and cost-effective manner. In particular, the apparatus and method according to the invention provide more accurate data than conventional methods such as in situ dynamic plate testing, static plate testing or California Bearing Ratio (CBR) testing, and are simpler and more cost-effective than repeated load tri-axial testing. In addition, samples of material can be prepared and stored in the container for a period of time before being engaged with the housing for testing.

Using the apparatus according to the invention, mechanical property data (eg elastic stiffness and permanent strain) may be obtained under repeated loading for unbound and lightly-bound material. This may not be possible using conventional methods as such material may collapse under loading if not supported. The fact that using the method and apparatus of the invention the material under test is only partially confined means that the measured behaviour more accurately reflects that to be expected on site.

The second face, or part of the second face, that is resiliently displaceable in use, is preferably a panel that is releasably fixable relative to the remainder of the sample container. The container preferably comprises a pair of opposed releasably fixable panels that form part of the wall of the container. Most preferably, the container has the form of a square or rectangular box having an open upper face, a square or rectangular base, one pair of opposed side walls that are fixed to the base, and a pair of opposed rectangular panels that constitute the other side walls of the container and are releasably secured to the rest of the container.

Thus, the container preferably has the form of an open-topped box. At least one, and more preferably an opposed pair, of the side walls of the box are, in use, displaceable outwardly in response to the compressive force applied via the open top of the container.

Most preferably, the releasable panels that make up one, or more preferably two, of the sides of the container can be clamped to the rest of the container, so that the panels are held in place prior to a measurement being made.

Once the container has been engaged with the housing, the panels are released from the container so as to be displaceable in response to deformation of the sample of material. Most preferably, the housing includes resilient means that engage each panel, displacement of each panel taking place against the action of the resilient means.

The container is preferably provided with handles, and is preferably less than about 30 kg in weight when charged with a sample of material, thereby facilitating manual handling of the container during use. Preferably, the container is constructed from stainless steel plate having a thickness of between 4 and 8 mm, for example about 6 mm. The internal surfaces of the container are preferably lined with a layer of material having a lower coefficient of friction than steel, such as polytetrafluoroethylene (PTFE), thereby reducing the coefficient of friction between the container and the sample of material. The layer of low-friction material is preferably less than 1 mm in thickness, and most preferably less than 0.6 mm in thickness.

The sample of material may be any material that can be packed with a close fit into the container. In the field of road and pavement construction, however, the material is most likely to comprise soil or aggregate with or without a suitable binder, such as lime, cement or bitumen. If the material includes a binder, the material is preferably introduced into the container while the binder is uncured. The sample of material is most preferably compacted within the container, and then any binder may be allowed to cure, so as to give the sample of material a form similar to that of the material in situ in a road or the like. In addition, water may be added to the sample of material before testing so as to simulate drainage or saturation conditions.

Preferably, means are provided for compacting the sample of material before the container is engaged with the housing. Such means preferably takes the form of a conventional vibrating hammer.

Most preferably, a compaction jacket is provided for supporting the walls of the container while the sample of material is compacted. The compaction jacket is preferably removed after compaction and prior to the container being engaged with the housing.

The compaction jacket is preferably adapted to fit closely about the walls of the container. Where the container has the form of a box having an open upper face, the compaction jacket preferably has opposed walls of variable separation. In particular, opposed walls of the compaction jacket are preferably mounted for at least a limited range of movement relative to the other walls, and the compaction jacket preferably includes means, eg threaded rods and tightening nuts, for drawing the walls into close abutment with the container. In use, therefore, the container is introduced into the compaction jacket, or the compaction jacket is fitted about the container, and the walls of the compaction jacket are urged into abutment with the sample container to provide support thereto during compaction.

The functionality of the sample container, such that the sides can be fixed for compaction, but the second face released for testing, greatly enhances the possible throughput of samples that can be tested compared with conventional techniques, and reduces costs.

The housing preferably includes means for fixing the container within the housing. Most preferably, the housing is provided with means for clamping the container within the housing, for example clamping bolts that are threadably engaged with a wall of the housing. In addition, the housing is preferably fixed relative to the means by which a compressive force is applied to the sample during use.

The housing preferably includes resilient means that engage each panel of the container, during use, so that each panel moves resiliently relative to the housing. The resilient means preferably comprises an abutment plate that is resiliently mounted relative to a wall of the housing, and that engages a panel of the container during use. Preferably, the resilient means comprises one or more resilient members, such as compression springs, that act between the abutment plate and either a wall of the housing or a component that is fixed, during use, relative to a wall of the housing.

In a preferred embodiment, the one or more resilient members act between the abutment plate and an intermediate plate that is fixed, during use, relative to a wall of the housing. In this case, the intermediate plate is preferably mounted relative to a wall of the housing such that the separation of the intermediate plate from the wall of the housing is variable. The variable separation is preferably achieved by means of the intermediate plate being slidably mounted relative to a wall of the housing, and a separation member that is threadably engaged to either a wall of the housing or a component that is fixed relative to the housing determining the separation of the intermediate plate from the wall of the housing. In this way, the separation of the intermediate plate from the wall of the housing may be increased until the abutment plate engages with a panel of the container. Most preferably, the stiffness of the one or more resilient members is adjustable.

Preferably, the housing has the form of a rectangular box with an open upper face through which the container is received. Preferably, the housing is constructed from stainless steel plate having a thickness of between 4 and 8 mm, for example about 6 mm. The walls of the housing may be strengthened with strengthening components that are fixed to the outer surface of the walls of the housing. For example, longitudinally orientated strengthening ribs, eg square-section steel tubing, may be fixed to the walls of the housing, and strengthening rings may be fixed about any openings in the walls of the housing. In order to facilitate the removal of any liquids that would otherwise accumulate within the housing, one or more drainage holes may be provided in the base of the housing.

The means for applying a compressive force to the sample of material may be generally conventional. Such means preferably comprises a loading plate for contacting the sample of material, a loading ram for applying force to the loading plate, and a loading frame to which the housing is fixed. Most preferably, the means for applying a compressive force to the sample of material takes the form of similar means used in conventional apparatus such as a Nottingham Asphalt Tester. The compression means is preferably computer controlled using suitable software, and is preferably capable of applying loads up to around 10 kN. Most preferably, the compression means is capable of applying repeated loads, in particular repeated loads of a predetermined magnitude, duration and frequency of repetition. The loading plate is preferably connected to the loading ram by a half-ball connector to ensure an even contact between the loading plate and the sample of material.

Deformation of the sample of material is preferably measured by measuring the displacement of each resiliently-displaceable panel of the sample container and/or the displacement of a loading plate of the compression means during testing. Most preferably, both the displacement of each panel and the displacement of the loading plate of the compression means is measured. Each displacement is most preferably measured using at least one linear displacement transducer, which is most preferably a Linear Variable Differential Transformer (LVDT). Each linear displacement transducer preferably communicates with a microcomputer which conducts analysis of the data received. In particular, the microcomputer preferably calculates, from the data received from the linear displacement transducers, any one of the elastic stiffness, the permanent shear strain, and the permanent volumetric strain, of the sample of material.

For each test, a range of different stress levels are preferably applied to the sample of material. Most preferably, each stress level corresponds to a different layer of the road or pavement for which the material is intended. For example, the stress levels applied to the sample of material might range from 50 to 200 kPa, and three or more different stress levels may be applied to each sample of material.

The invention will now be described in greater detail, by way of illustration only, with reference to the accompanying drawings, in which

DETAILED DESCRIPTION OF THE DRAWINGS

Figure 1:
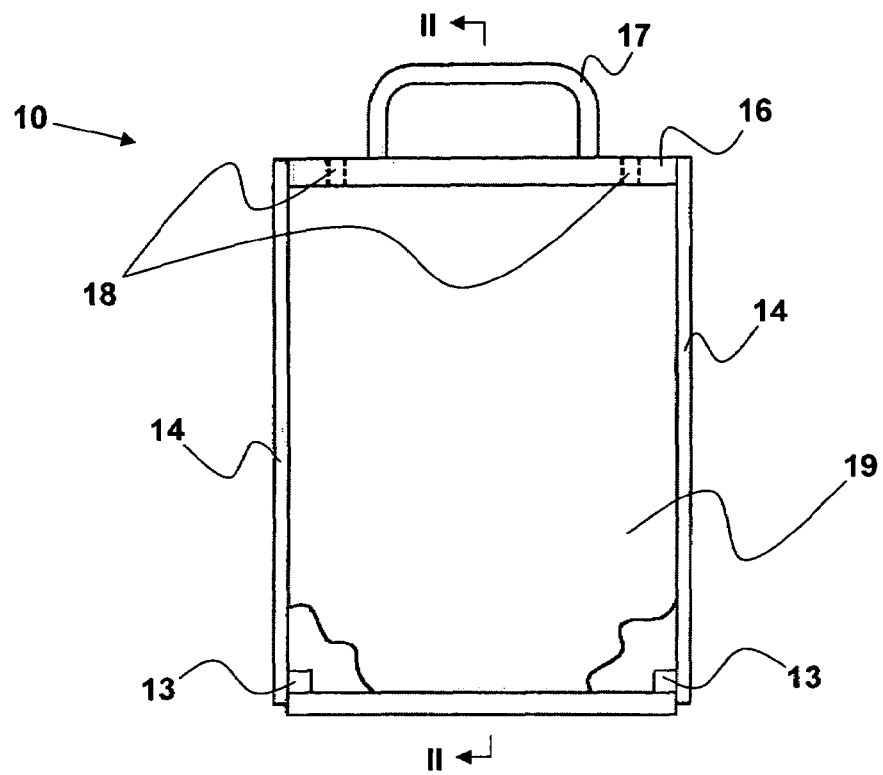
FIG. 1 is an end view, partially cut away, of a sample container, which forms part of material testing apparatus according to the invention.
Figure 2:
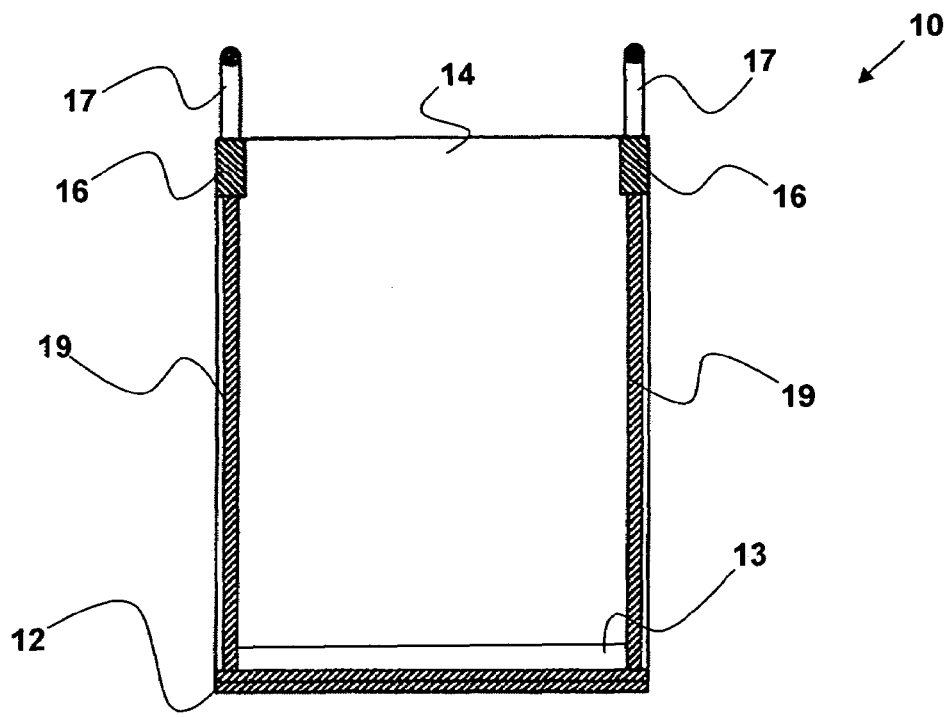
FIG. 2 is a sectional view, along the line II—II in FIG. 1, of the sample container.
Figure 4:
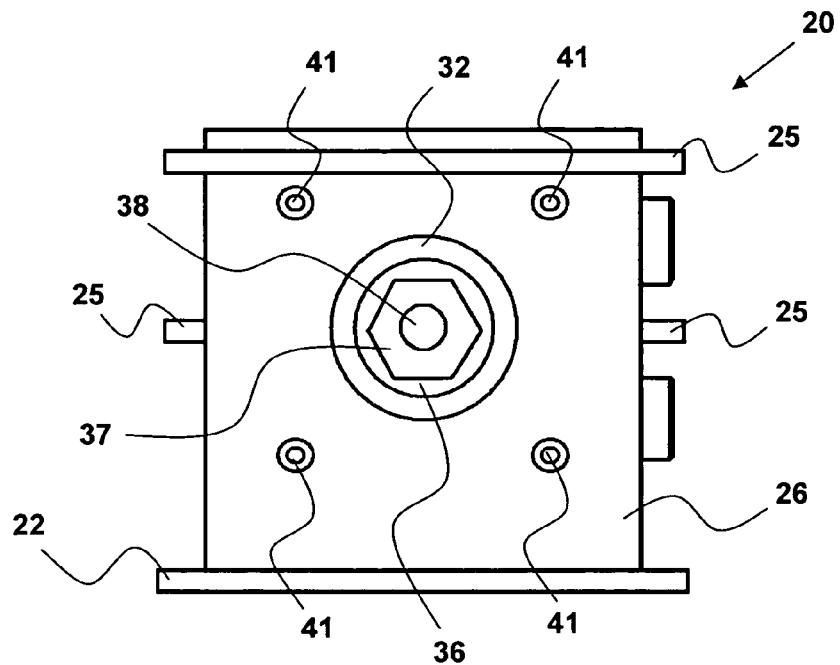
FIG. 4 is an end view of the test housing.
Figure 5:
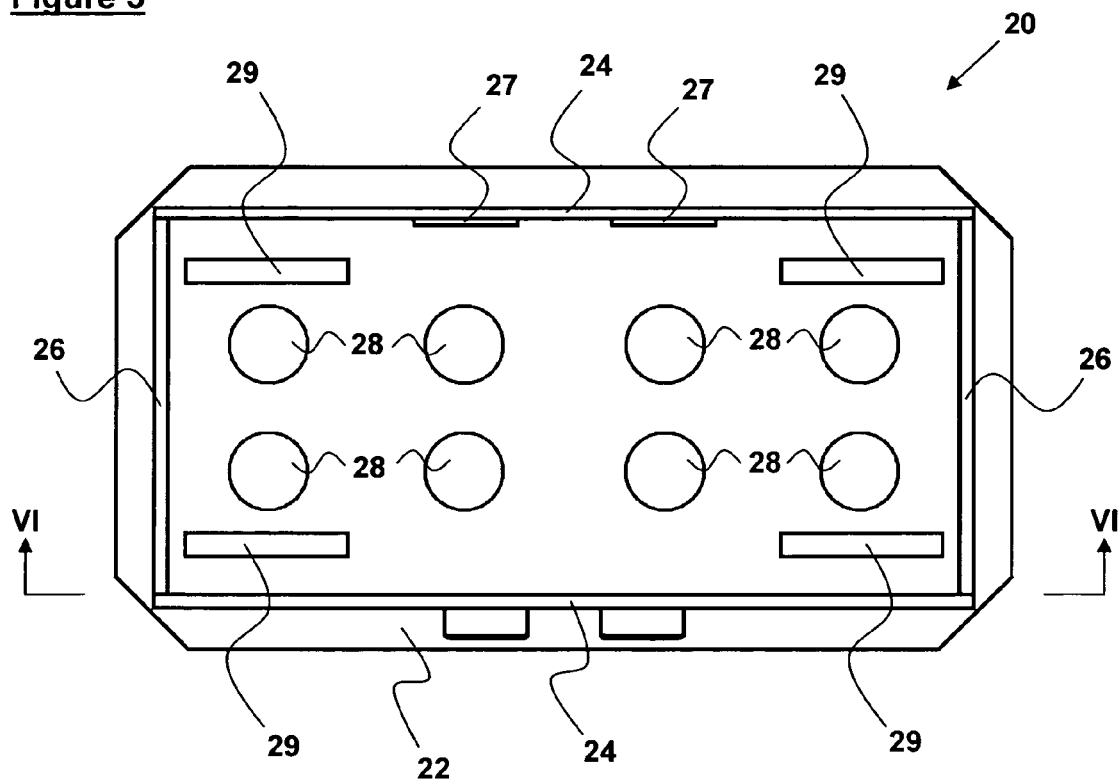
FIG. 5 is a plan view of the test housing with spring-loaded members removed for clarity.
Figure 6:
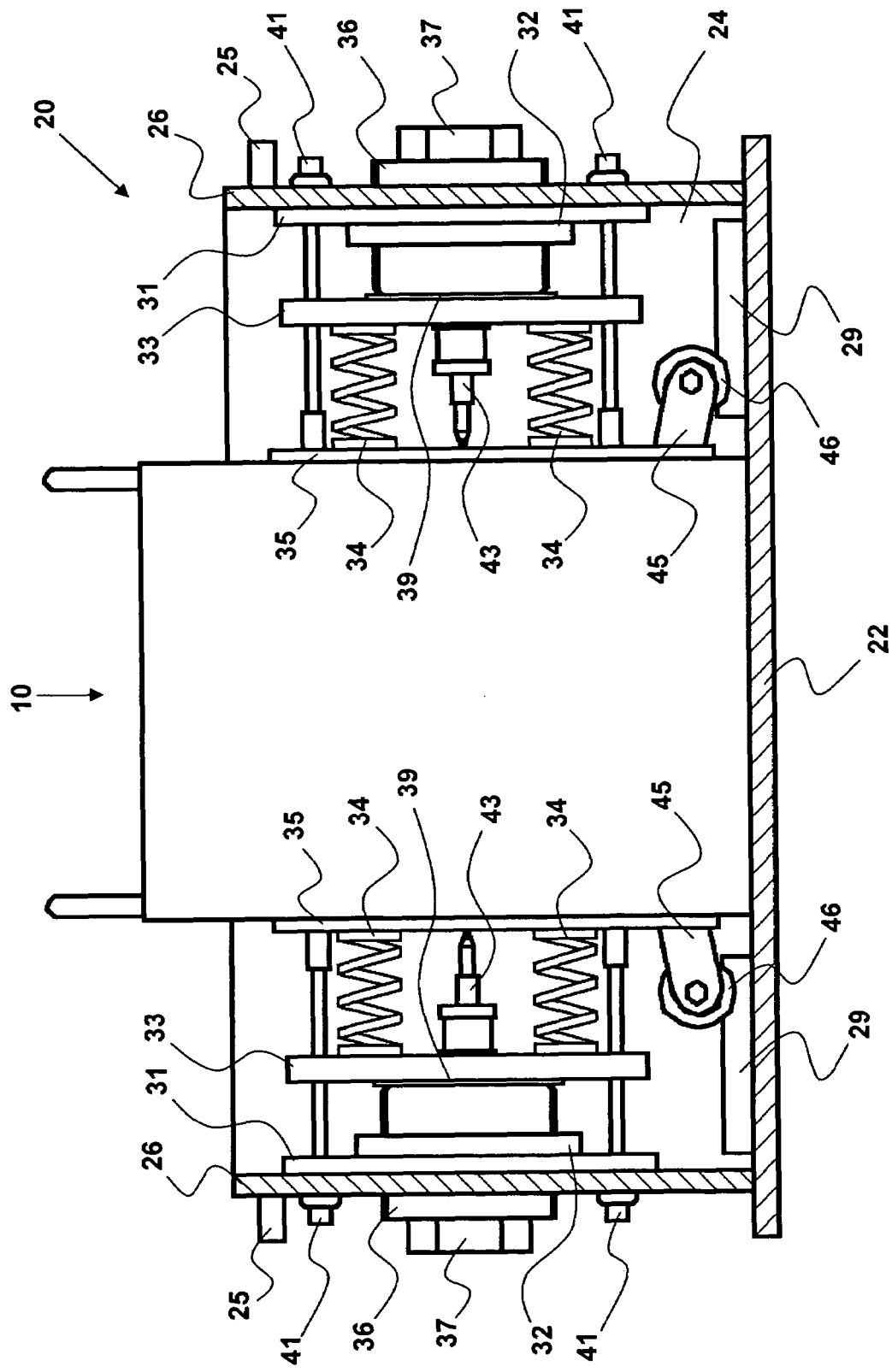
FIG. 6 is a sectional view of the material testing apparatus, along the line VI—VI in FIG. 5, with the spring-loaded members and sample container in place.

Material testing apparatus according to the invention is shown in FIG. 6, and comprises a sample container 10, as shown in FIGS. 1, 2 and 6, and a test housing 20, as shown in FIGS. 3 to 6.

The sample container 10 is of square cross-section, with a side of 170 mm, and is adapted to contain compacted material in the form of a cube or cuboid. The sample container 10 enables the material to be compacted, and cured if necessary, whilst contained within the sample container 10. The material can then be stored within the sample container 10, if necessary for a protracted period of time, and introduced into the test housing 20 only when a measurement is to be made. The sample container 10 is formed from stainless steel having a thickness of 6 mm, and comprises a base 12, a pair of upstanding side walls 14 fixed to either side of the base 12 and supported by a pair of square-section supports 13, and a pair of struts 16 of rectangular cross-section that extend between the upper ends of the two side walls 14. The upper surface of each strut 16 has a handle 17 extending upwardly therefrom, which allows the sample container 10 to be transported manually. Finally, a removable panel 19 is clamped between the lower surface of each strut 16 and the upper surface of the base 12 using clamping screws (not shown in the Figures) engaged with a pair of threaded bores 18 formed vertically (as viewed in FIGS. 1 and 2) through each strut 16.

The removable panels 19 fit between the ends of the side walls 14 with a clearance at each side of about 1 mm. The force exerted by the clamping screws is sufficient to hold the panels 19 in place during storage of the sample container 10. When the clamping screws are removed or loosened, however, the panels 19 become loose and are thereby released from the rest of the container 10.

The sample container 10 thus has the general form of an open-topped box with a pair of facing walls 14 fixed to the base 12, and a pair of removable end walls in the form of the panels 19.

In use, membranes of polytetrafluoroethylene (PTFE) are interposed between the sample and the inwardly facing surfaces of the sample container 10, in order to reduce the coefficient of friction between the sample and the sample container 10 (the PTFE membranes are not shown in the Figures). The PTFE membrane has a thickness of 0.5 mm, it having been found that particles from the sample of material are liable to embed themselves in layers of PTFE of greater thickness. In addition, the PTFE membrane extends around the sides of the movable panels 19 so as to reduce the risk of particles from the sample entering the space between the side walls 14 and the movable panels 19, and inhibiting their relative movement.

Figure 7:
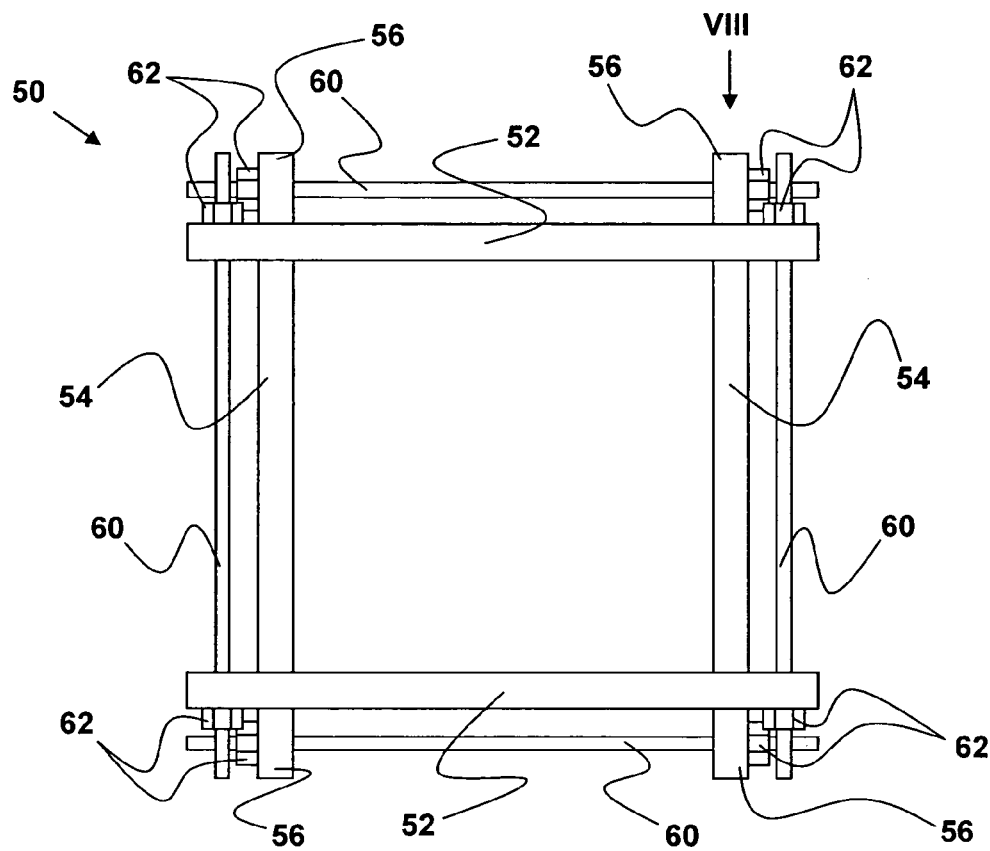
FIG. 7 is a plan view of a compaction jacket used in association with the sample container of FIGS. 1 and 2.
Figure 8:
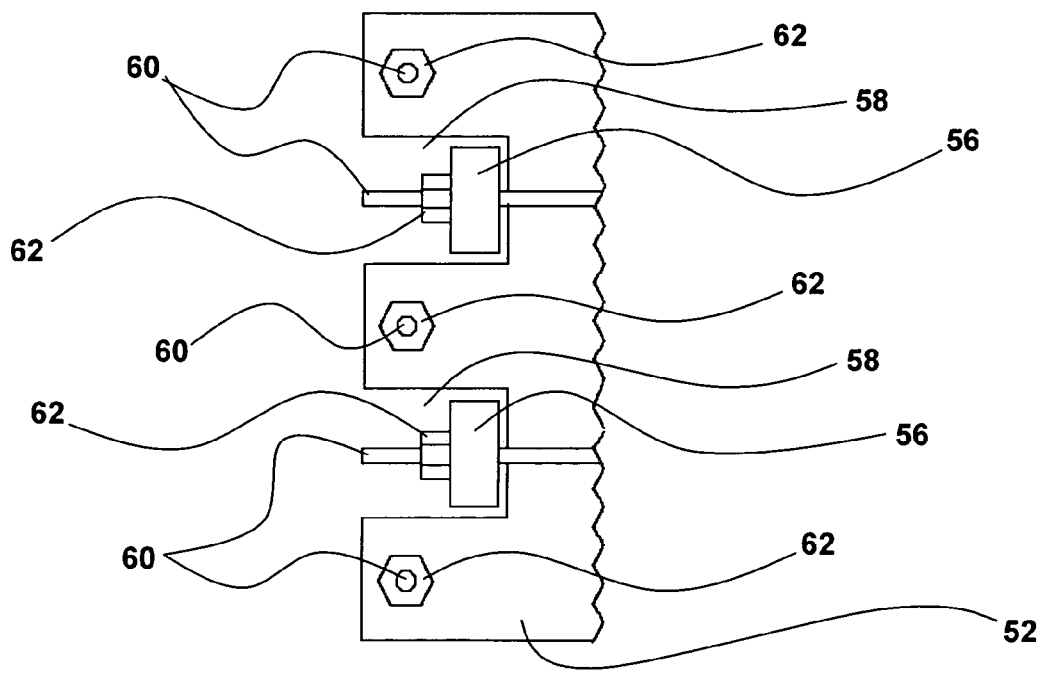
FIG. 8 is a fragmentary detail on the arrow VIII of FIG. 7.

Once a sample of material has been introduced into the sample container 10, the sample is compacted. In order to compact the sample of material, the sample container 10 is inserted into a compaction jacket (as shown in FIGS. 7 and 8). The compaction jacket is generally designated 50, and comprises a pair of opposing end walls 52 and a pair of opposing side walls 54. The side walls 54 are formed at each side with two extensions 56 that are received within corresponding slots 58 formed at the sides of the end walls 52. The extensions 56 of the side walls 54 are slidable within the corresponding slots 58 of the end walls 52 so that opposing walls 52,54 of the jacket 50 are movable relative to each other. The extensions 56 of the side walls 54 each contain a bore through which threaded rods 60 extend. Similarly, the portions of the end walls 52 situated between the slots 58 each contain a bore through which threaded rods 60 extend. Tightening nuts 62 are fitted to each end of the rods 60, such that by rotating the nuts 62, opposing walls 52,54 of the jacket 50 can be drawn towards each other.

The sample container 10 is introduced into the compaction jacket 50, and the walls 52,54 of the compaction jacket 50 are urged into abutment with the sample container 10 by tightening of the nuts 62. Sample material may be introduced into the sample container 10 either before or after the container 10 is engaged with the compaction jacket 50. A vibrating hammer is then used to compact the sample of material as required. The compaction jacket 50 prevents the sample container 10 from being deformed during the compaction process. After compaction, the tightening nuts 62 are loosened and the sample container 10 removed from the compaction jacket 50.

The test housing 20, as shown in FIGS. 3, 4, 5, and 6 has the general form of a rectangular open-topped box, and is adapted to receive the sample container 10, as shown in FIG. 6. The test housing 20 comprises a rectangular base 22, side walls 24, and end walls 26. The base 22 and walls 24,26 of the test housing 20 are formed from stainless steel and each have a thickness of 6 mm. The base 22 extends outwardly beyond the lower ends of the walls 24,26 so as to form a peripheral flange.

Figure 3:
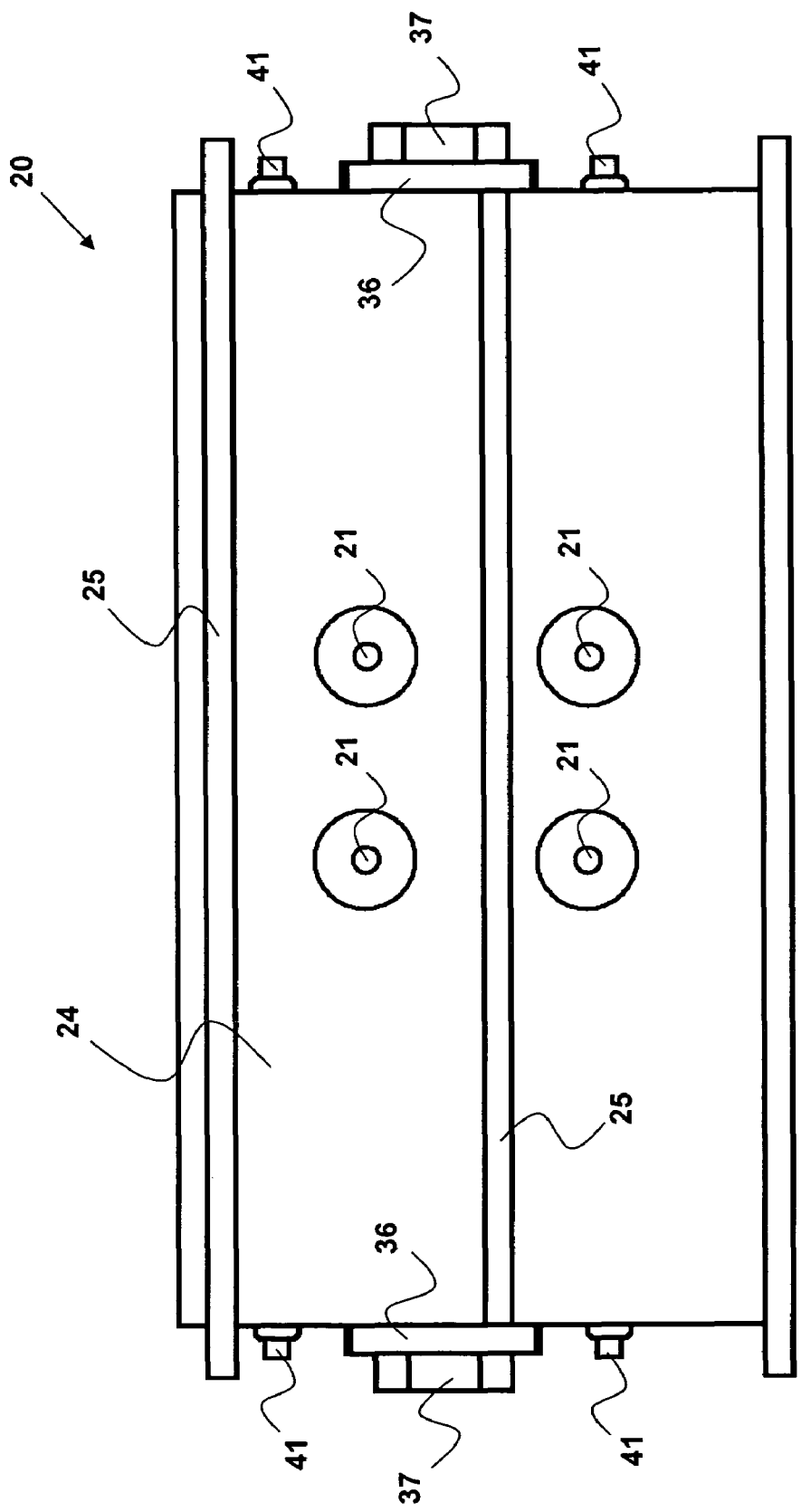
FIG. 3 is a side view of a test housing that forms part of material testing apparatus according to the invention.

In order to enhance the strength of the test housing 20, several lengths of square-section stainless steel tubing 25 are fixed to the outer surfaces of the walls 24,26. In particular, the outer surface of each side and end wall 24,26 has a single length of tubing 25 disposed along its upper portion, and the outer surface of each side wall 24 has a length of tubing 25 disposed along its centre, as shown in FIGS. 3 and 4. The stainless steel tubing has been omitted from FIG. 5 for clarity. The test housing 20 is formed by welding the base 22, walls 24,26 and tubing 25 together.

The test housing 20 has a weight of approximately 20 kg, so manual handling of the test housing 20 is possible. The lengths of square-section steel tubing 25 facilitate such handling but handles (not shown in the Figures) may also be provided at each end of the test housing 20.

Each end wall 26 of the test housing 20 has a central bore formed therein within which part of a spring-loaded member is received. Four relatively smaller bores are also formed in each end wall 26 in a square arrangement about the central bore. The spring-loaded members are described in more detail below with reference to FIG. 6.

One of the side walls 24 of the test housing 20 has four threaded bores 21 formed therein. The four threaded bores 21 are arranged in a square arrangement about the centre of the side wall 24. Stainless steel rings are welded to the outer surface of the test housing 20 around each threaded bore 21 to provide additional strength about each bore 21, and increase the length of the thread. The other side wall 24 of the test housing 20 has a pair of vertically-orientated rectangular plates 27 that are welded to its interior surface, as shown in FIG. 5. In addition, the base 22 of the test housing 20 is formed with a regular array of eight drainage holes 23, as shown in FIG. 5, that prevent accumulation of liquid within the test housing 20.

FIG. 6 shows a side view of the testing apparatus with the nearest side wall 24 of the test housing 20 removed. As shown in FIG. 6, the sample container 10 is introduced into the test housing 20 in an upright orientation. The sample container 10 and a typical sample of material will generally have a combined weight of approximately 20 kg, and will therefore be light enough to be introduced into the test housing 20 manually. The sample container 10 is orientated within the test housing 20 so that the movable panels 19 of the sample container 10 face the end walls 26 of the test housing 20, one of the side walls 14 of the sample container 10 abuts the rectangular plates 27, and the other side wall 14 of the sample container 10 is disposed alongside but not quite in contact with the adjacent side wall 24 of the test housing 20.

Threaded bolts (not shown in the Figures), which have enlarged heads adapted to be engaged and rotated by a suitable tool, are engaged with the threaded bores 21 of the test housing 20 so as to contact one side 14 of the sample container 10, thereby fixing the sample container 10 within the test housing 20.

A spring-loaded member is engaged with each end wall 26 of the test housing 20. Each spring-loaded member comprises an outer plate 31 that is disposed alongside the interior surface of an end wall 26 of the test housing 20, an intermediate plate 33 that is slidably mounted relative to the outer plate 31, and an abutment plate 35 that is resiliently mounted by means of four springs 34 (only two are visible in FIG. 6) to the intermediate plate 33 and is disposed alongside and in contact with a movable panel 19 of the sample container 10 during use. Each spring-loaded member is formed principally from aluminium.

The outer plate 31 includes a central cylindrical formation 32 that is received within the central bore of the end wall 26 of the test housing 20 such that the remainder of the outer plate 31 lies alongside the interior surface of the end wall 26 during use. A co-axial threaded bore is formed within the cylindrical formation 32 of the outer plate 31, and a cylindrical separation member 36 with a threaded external surface is engaged with the threaded bore of the outer plate 31. The outer end of the separation member 36 includes a hexagonal formation 37 that is engaged by a suitable tool, in use, in order to rotate the separation member 36. A bore 38 extends co-axially through the separation member 36, and the inner end of the separation member 36 abuts the outer surface of the intermediate plate 33 during use.

The intermediate plate 33 and abutment plate 35 are slidably mounted relative to the outer plate 31 by means of four guide rods 41. The guide rods 41 are fixed to the abutment plate 35, and extend through corresponding bores formed in corner portions of the intermediate plate 33 and the outer plate 31, and through bores 41 in the end wall 26 of the test housing 20. The outwardly-facing surfaces of the abutment plate 35 and the outer plate 31 include cylindrical guide formations through which the guide rods 41 extend. The guide formations of the outer plate 31 are received within bores 41 of the end wall 26. In addition, each guide rod 41 includes an enlarged head that is situated externally of the test housing 20, and is adapted to abut the corresponding guide formation of the outer plate 31 when the guide rod 41 is in its most inwardly-displaced configuration, as shown in FIG. 6.

The location of the intermediate plate 33 relative to the outer plate 31 and the abutment plate 35 is determined by the separation member 36 and the springs 34, respectively. A linear displacement transducer, and in particular a Linear Variable Differential Transformer (LVDT) 43, is mounted within a central bore of the intermediate plate 33. The LVDT 43 comprises a housing that is fixedly mounted within the central bore of the intermediate plate 33, and a movable member that extends into abutment with the abutment plate 35 during use. The housing of the LVDT 43 extends into a cavity within the separation member 36, and the inner end of the separation member 36 abuts a brass annular plate 39 that is mounted on the surface of the intermediate plate 33. The annular plate 39 facilitates rotation of the separation member 36 during use. Power and data cables for the LVDTs 43 pass into the test housing 20 through the bore 38 of the separation member 36.

The abutment plate 35 is adapted to engage a panel 19 of the sample container 10. The four springs 34 are arranged regularly about the LVDT 43, and each extend between the intermediate plate 33 and the abutment plate 35 so that the abutment plate 35 is resiliently movable relative to the intermediate plate 33.

The abutment plate 35 includes a pair of brackets 45 at its lower end, and a guide roller 46 mounted to each bracket 45. Each guide roller 46 has low-friction bearings, and is formed with a V-shaped recess about its circumference within which it receives a guide rail 29 that is formed on the base of the test housing 20. The guide rollers 46 and low-friction bearings are formed from plastics material. The guide rails 29 and guide rollers 46 act to support the spring-loaded member, and facilitate low-friction movement of the abutment plate 35.

After the sample container 10 has been positioned within the housing 20, the clamping screws that pass through the struts 16 are loosened, thereby releasing the panels 19 from the remainder of the sample container 10.

Means are provided for imparting a compressive force to the sample of material within the sample container 10. Such means (not shown in the Figures) conveniently take the form of corresponding elements of apparatus such as a Nottingham Asphalt Tester which has a loading frame suitable for engaging the test housing 20, and a loading plate adapted to contact the entire upper surface of the sample of material within the sample container 10. The loading frame may include a plurality of clamps that clamp the peripheral flange of the test housing 20 to the loading frame during use. The loading plate is connected to a loading ram such that repeated compression loads can be applied to the sample of material. The loading ram and loading plate are connected by a half-ball connector to ensure that there is an even contact between the loading plate and the upper surface of the sample of material. In addition, the material testing apparatus comprises two vertically orientated LVDTs (not shown in the Figures), which measure the displacement of the loading plate relative to the sample container 10.

The four LVDTs 43 of the testing apparatus allow the movement of the loading plate and the movable panels 19 relative to the test housing 20 to be measured during testing. The data provided by the LVDTs 43 is processed to provide information regarding the deformation, and hence the mechanical properties, of the sample of material.

In use, the movable panels 19 of the sample container 10 are initially clamped between the base 12 and struts 16 of the sample container 10, and material to be tested is introduced into the sample container 10. Typically, the material will comprise a soil or aggregate and possibly also a binder, such as uncured cement or bitumen. Once the material has been introduced into the sample container 10, the sample container 10 is placed into the compaction jacket, as described above, so as to support the base 12, side walls 14 and movable panels 19 of the sample container 10. A conventional vibrating hammer (not shown in the Figures) is then used to compact the sample of material, as described above. The sample of material should then have a form similar to that of the material as used in a road or the like. The sample of material may be stored in the sample container 10 for a period of time until testing is ready to be carried out. For example, the sample may be stored for a protracted period while the binder is allowed to cure. It may also be desired to introduce moisture into the sample of material before testing so that drainage or saturation conditions can be investigated.

In order to test the prepared sample of material, the sample container 10 is placed inside the test housing 20 which is clamped into a loading frame similar to that of a Nottingham Asphalt Tester. Bolts are engaged with the appropriate side wall 24 of the test housing 20 so as to fix the sample container 10 within the test housing 20. The separation members 36 of the spring-loaded members are then rotated so that the abutment plates 35 are brought into contact with the movable panels 19 of the sample container 10 with zero stress being imparted on the movable panels 19. Data from the horizontally-orientated LVDTs 43 is used to ensure that the abutment plates 35 engage the movable panels 19 with zero stress. The movable panels 19 are unclamped from the base 12 and struts 16 of the sample container 10 so that they are able to move relative to the remainder of the sample container 10 and the test housing 20.

The loading plate is then brought into contact with the upper surface of the sample of material within the sample container 10, and used to apply repeated compression loads to the sample of material. The pressure applied to the sample of material by the compression load is commonly referred to as the stress (measured in Pascals, Pa). Due to the non-linear behaviour of most materials suitable for pavement construction, a range of different stress levels are applied to the sample of material to simulate the stress encountered at different depths in a pavement. For example, a testing procedure might comprise the steps of applying 1000 compression loads at a low stress level (eg 50 kPa), applying 1000 compression loads at an intermediate stress level (eg 100 kPa), and applying 1000 compression loads at a high stress level (eg 150 kPa). The loading plate is controlled using a microcomputer which also receives and analyses measurements from the LVDTs 43 of the material testing apparatus.

The two vertically mounted LVDTs 43, and the two horizontally mounted LVDTs 43, then measure the resulting movement of the loading plate and the two movable panels 19, and transmit data to the microcomputer for analysis. The microcomputer uses the data supplied by the LVDTs 43 to calculate the elastic stiffness (MPa), and the permanent shear and volume strain (%), of the sample of material. An accurate picture of the stiffness of the material, and the material's resistance to permanent shear and volumetric deformation, can therefore be established.

Examples of materials that are suitable for testing using the apparatus and method according to the invention are:

(a) Clays and clay-like or clay-containing materials;
(b) Lime stabilised clay;
(c) Granular materials;
(d) Hydraulically bound materials;
(e) Foamed bitumen or emulsion bound materials.

The above materials may be tested with various moisture contents, with different levels of binder content, under different curing regimes, and at different ages.

The invention claimed is:

1. Apparatus for testing the mechanical properties of a material, which apparatus comprises a sample container adapted to be filled with a sample of the material and then engaged with a housing such that the sample container is, in use, fixedly mounted within the housing, the sample container having a first, open face via which a compressive load can be applied to the sample and a second face disposed orthogonally to the first, open face, at least a portion of said second face being resiliently displaceable, outwardly of the sample container, in response to deformation of the sample brought about by application of the load, wherein the second face, or the portion of the second face, that is resiliently displaceable in use is a panel that is releasably fixable relative to the remainder of the sample container, and the housing includes a resilient mechanism that engages the panel, displacement of the panel taking place against the action of the resilient mechanism.

2. Apparatus as claimed in claim 1, wherein the sample container comprises a pair of opposed releasably fixable panels that form part of the wall of the sample container.

3. Apparatus as claimed in claim 2, wherein the sample container has the form of a square or rectangular box having an open upper face, a square or rectangular base, one pair of opposed side walls that are fixed to the base, and a pair of opposed rectangular panels that constitute the other side walls of the container and are releasably secured to the rest of the container.

4. Apparatus as claimed in claim 1, wherein means are provided for compacting the sample of material before the sample container is engaged with the housing.

5. Apparatus as claimed in claim 4, wherein a compaction jacket is provided for supporting the walls of the sample container while the sample of material is compacted.

6. Apparatus as claimed in claim 4, wherein a compaction jacket is provided for supporting the walls of the sample container while the sample of material is compacted, and the compaction jacket is adapted to fit closely about the walls of the sample container.

7. Apparatus as claimed in claim 4, wherein the container has the form of a box having an open upper face, a compaction jacket is provided for supporting the walls of the sample container while the sample of material is compacted, and the compaction jacket has opposed walls of variable separation.

8. Apparatus as claimed in claim 7, wherein a compaction jacket is provided for supporting the walls of the sample container while the sample of material is compacted, and opposed walls of the compaction jacket are mounted for at least a limited range of movement relative to the other walls, and the compaction jacket includes means for drawing the walls into close abutment with the sample container.

9. Apparatus as claimed in claim 1, wherein the resilient means comprises an abutment plate that is resiliently mounted relative to a wall of the housing, and engages a panel of the sample container during use.

10. Apparatus as claimed in claim 1, wherein the resilient means comprises one or more resilient members, such as compression springs, that act between the abutment plate and either a wall of the housing or a component that is fixed, during use, relative to a wall of the housing.

11. Apparatus as claimed in claim 1, wherein the resilient means comprises one or more resilient members that act between the abutment plate and an intermediate plate that is fixed, during use, relative to a wall of the housing.

12. Apparatus as claimed in claim 11, wherein the resilient means comprises one or more resilient members that act between the abutment plate and an intermediate plate that is fixed, during use, relative to a wall of the housing, and the intermediate plate is mounted relative to a wall of the housing such that the separation of the intermediate plate from the wall of the housing is variable.

13. Apparatus as claimed in claim 12, wherein the resilient means comprises one or more resilient members that act between the abutment plate and an intermediate plate that is fixed, during use, relative to a wall of the housing, the intermediate plate is mounted relative to a wall of the housing such that the separation of the intermediate plate from the wall of the housing is variable, and the variable separation is achieved by means of the intermediate plate being slidably mounted relative to a wall of the housing, and a separation member that is threadably engaged to either a wall of the housing or a component that is fixed relative to the housing determining the separation of the intermediate plate from the wall of the housing.

14. Apparatus as claimed in claim 1, wherein the housing is provided with means for clamping the sample container within the housing.

15. Apparatus as claimed in claim 1, wherein the housing has the form of a rectangular box with an open upper face through which the container is received.

16. Apparatus as claimed in claim 1, wherein one or more drainage holes are provided in the base of the housing.

17. Apparatus as claimed in claim 1, wherein the means for applying a compressive force to the sample of material comprises a loading plate for contacting the sample of material, a loading ram for applying force to the loading plate, and a loading frame to which the housing is fixed.

18. Apparatus as claimed in claim 1, wherein the loading plate is connected to the loading ram by a half-ball connector.

19. Apparatus as claimed in claim 1, wherein the means for applying a compressive force to the sample of material is capable of applying repeated loads.

20. Apparatus as claimed in claim 19, wherein the means for applying a compressive force to the sample of material is capable of applying repeated loads of a predetermined magnitude, duration and frequency of repetition.

21. Apparatus as claimed in claim 1, wherein deformation of the sample of material is measured by measuring the displacement of each resiliently-displaceable panel of the sample container and/or the displacement of a loading plate of compression means during testing.

22. Apparatus as claimed in claim 21, wherein both the displacement of each panel and the displacement of the loading plate of the compression means is measured during testing.

23. Apparatus as claimed in claim 21, wherein each displacement is measured using at least one linear displacement transducer.

24. Apparatus as claimed in claim 21, wherein each displacement is measured using at least one Linear Variable Differential Transformer.

25. Apparatus as claimed in claim 21, wherein each displacement is measured using at least one linear displacement transducer that communicates with a microcomputer which conducts analysis of the data received.

26. Apparatus as claimed in claim 21, wherein each displacement is measured using at least one linear displacement transducer that communicates with a microcomputer, and the microcomputer calculates, from the data received from the linear displacement transducers, any one of the elastic stiffness, the permanent shear strain, and the permanent volumetric strain, of the sample of material.

27. A method of testing the mechanical properties of a material, which method comprises the following steps:
    (a) providing an apparatus comprising a housing and a sample container, the sample container having a first, open face via which a compressive load can be applied to a sample and a second face disposed orthogonally to the first, open face, at least a portion of said second face being resiliently displaceable, outwardly of the sample container, in response to deformation of the sample brought about by application of the load, wherein the second face, or the portion of the second face, that is resiliently displaceable in use is a panel that is releasably fixable relative to the remainder of the sample container;
    (b) introducing a sample of the material into the sample container;
    (c) engaging the sample container with the housing such that the sample container is fixedly mounted within the housing;
    (d) engaging the panel with a resilient mechanism of the housing such that displacement of the panel takes place against the action of the resilient mechanism;
    (e) applying a compressive force to the sample; and
    (f) measuring movement of the panel in response to said compressive force.

28. A method as claimed in claim 27, wherein the sample of material is compacted before the sample container is engaged with the housing.

29. A method as claimed in claim 27, wherein the sample of material is compacted before the sample container is engaged with the housing, and a compaction jacket supports the walls of the sample container while the sample of material is compacted, and the compaction jacket is removed after compaction and prior to the sample container being engaged with the housing.

30. A method as claimed in claim 27, wherein the sample of material comprises soil or aggregate.

31. A method as claimed in claim 30, wherein the sample of material includes a binder.

32. A method as claimed in claim 30, wherein the sample of material includes a binder, and the material is introduced into the container while the binder is uncured, the sample of material is compacted within the sample container, and then any binder is allowed to cure.

33. A method as claimed in claim 27, wherein movement of the resiliently-displaceable second face, or resiliently-displaceable portion thereof, is measured using at least one linear displacement transducer.

34. A method as claimed in claim 33, wherein each linear displacement transducer is a Linear Variable Differential Transformer (LVDT).

35. A method as claimed in claim 33, wherein each linear displacement transducer communicates with a microcomputer which conducts analysis of the data received.

36. A method as claimed in claim 33, wherein each linear displacement transducer communicates with a microcomputer, and the microcomputer calculates, from the data received from the linear displacement transducers, any one of the elastic stiffness, the permanent shear strain, and the permanent volumetric strain, of the sample of material.

37. A method as claimed in claim 27, wherein three or more different stress levels are applied to each sample of material.

38. A sample container for use in testing the mechanical properties of a material, the sample container being adapted to be filled with a sample of the material, and having a first, open face via which a compressive load can be applied to the sample and a second face disposed orthogonally to the first, open face, at least a portion of said second face being a panel that is releasably fixable relative to the remainder of the sample container and hence displaceable, outwardly of the sample container, in response to deformation of the sample during testing, wherein a compaction jacket is provided for supporting the sample container while the sample is compacted, the compaction jacket having opposed walls that are mounted for at least a limited range of movement relative to the other walls, and the compaction jacket including means for drawing the walls into close abutment with the sample container.

39. A sample container as claimed in claim 38, wherein the sample container comprises a pair of opposed releasably fixable panels that form part of the wall of the sample container.

40. A sample container as claimed in claim 38, wherein the sample container has the form of a square or rectangular box having an open upper face, a square or rectangular base, one pair of opposed side walls that are fixed to the base, and a pair of opposed rectangular panels that constitute the other side walls of the container and are releasably secured to the rest of the container.

41. A sample container as claimed in claim 38 wherein the compaction jacket is adapted to fit closely about the walls of the sample container.

* * * * *